US012585060B2

(12) United States Patent
Yu

(10) Patent No.: US 12,585,060 B2
(45) Date of Patent: Mar. 24, 2026

(54) LIGHT-EMITTING HEADPHONE STAND AND ITS COLUMNAR ILLUMINATION COMPONENT

(71) Applicant: AmTRAN Technology Co., Ltd., New Taipei City (TW)

(72) Inventor: Ming Chih Yu, Taipei City (TW)

(73) Assignee: AmTRAN Technology Co., Ltd., New Taipei City (TW)

( * ) Notice: Subject to any disclaimer, the term of this patent is extended or adjusted under 35 U.S.C. 154(b) by 284 days.

(21) Appl. No.: 18/328,771

(22) Filed: Jun. 5, 2023

(65) Prior Publication Data

US 2024/0288625 A1    Aug. 29, 2024

(30) Foreign Application Priority Data

Feb. 23, 2023    (TW) ................................. 112106811

(51) Int. Cl.
*A61L 2/10* (2026.01)
*F21V 8/00* (2006.01)
*F21V 33/00* (2006.01)

(52) U.S. Cl.
CPC ......... *G02B 6/0071* (2013.01); *G02B 6/0016* (2013.01); *G02B 6/0036* (2013.01); *G02B 6/0068* (2013.01); *G02B 6/0073* (2013.01); *G02B 6/0083* (2013.01); *A61L 2/10* (2013.01); *F21V 33/0056* (2013.01)

(58) Field of Classification Search
CPC .. G02B 6/0071; G02B 6/0016; G02B 6/0036; G02B 6/0068; G02B 6/0073; G02B 6/0083; A61L 2/10; F21V 33/0056
See application file for complete search history.

(56) References Cited

U.S. PATENT DOCUMENTS 6,177,667 B1 *  1/2001  Fujita ................... G02B 3/0037
                                                        359/627
7,942,565 B2 *  5/2011  Klick ................... G02B 6/0028
                                                        362/555
10,088,118 B2 * 10/2018  Naron ................... F21S 43/315
                (Continued)

FOREIGN PATENT DOCUMENTS

CN        104165287 A    11/2014
CN        108492739 A     9/2018
                (Continued)

*Primary Examiner* — Thomas A Hollweg
*Assistant Examiner* — Marc E Manheim
(74) *Attorney, Agent, or Firm* — CKC & Partners Co., LLC

(57)    ABSTRACT

A columnar illumination component includes a columnar body and a light-emitting component. The columnar body has two first side portions, and two second side portions. Each of the first side portions is adjoined to the second side portions, each of the second side portions is adjoined to the first side portions, and an elongated channel is jointly defined by the first side portions and the second side portions. The light-emitting component is located inside the elongated channel, and includes two light guides and two light source modules where the light guides are respectively fixed on the first side portions. The light source modules are respectively fixed on the second side portions, and each of the light source modules emits lights towards one of the light guides, and outputs the lights outwardly through the light guide.

10 Claims, 7 Drawing Sheets

(56)                    References Cited

U.S. PATENT DOCUMENTS

| | | | |
|---|---|---|---|
| 11,040,123 B2 * | 6/2021 | Li | A61L 9/20 |
| D1,036,401 S * | 7/2024 | Mai | D14/125 |
| 2001/0019487 A1 * | 9/2001 | Honguh | G02B 6/0061 |
| | | | 385/901 |
| 2008/0291514 A1 * | 11/2008 | Lin | H04N 1/028 |
| | | | 358/509 |
| 2013/0286679 A1 | 10/2013 | Chen et al. | |
| 2017/0241615 A1 * | 8/2017 | Luo | G02B 6/0068 |
| 2020/0056746 A1 * | 2/2020 | Xu | F21V 17/164 |
| 2022/0175998 A1 * | 6/2022 | Vargas | A61L 2/186 |

FOREIGN PATENT DOCUMENTS

| | | | |
|---|---|---|---|
| CN | 211787044 U | | 10/2020 |
| CN | 212391632 U | | 1/2021 |
| CN | 113613128 A | | 11/2021 |
| CN | 216905246 U | | 7/2022 |
| CN | 218064665 U | * | 12/2022 |
| TW | 200846601 A | | 12/2008 |
| TW | M460475 U | | 8/2013 |
| TW | M610109 U | | 4/2021 |
| TW | M633355 U | | 10/2022 |

* cited by examiner

A-A

LIGHT-EMITTING HEADPHONE STAND AND ITS COLUMNAR ILLUMINATION COMPONENT

RELATED APPLICATIONS

This application claims priority to Taiwan Application Serial Number 112106811, filed on Feb. 23, 2023, which is herein incorporated by reference in its entirety.

BACKGROUND

Field of Disclosure

The present disclosure relates to a headphone stand. More particularly, the present disclosure relates to a light-emitting headphone stand and its columnar illumination component which have visible light and disinfection light functions.

Description of Related Art

Recently, a headphone stand specially designed for headphones has launched on the markets, allowing users to hang their headphones on the headphone stand when the headphones are not in use.

However, some headphone stands on the markets are only positioned as peripheral devices for gaming products, and an optical design used therein is only capable of emitting colored lights in part or on single side of the headphone stand, thus, lacking more comprehensive light-emitting designs and more peripheral functions, and cannot meet the requirements of users in more usage scenarios.

Therefore, the above-mentioned technology apparently still has certain inconvenience and defects that need to be addressed through further refinement. Hence, developing effective solution to improve the foregoing shortcomings is currently one of the most important research and development tasks and a pressing goal for professionals working in this field.

SUMMARY

One aspect of the present disclosure is to provide a light-emitting headphone stand and its columnar illumination component for solving the difficulties mentioned above in the prior art.

In one embodiment of the present disclosure, a columnar illumination component is provided, and the columnar illumination component includes a columnar body and a light-emitting component. The columnar body has two first side portions and two second side portions. The first side portions are opposite to each other, and the second side portions are opposite to each other. Each of the first side portions is adjoined to the second side portions, and each of the second side portions is adjoined to the first side portions, and an elongated channel is jointly defined by the first side portions and the second side portions. The light-emitting component is located inside the elongated channel and includes two light guides and two light source modules, where the light guides are respectively fixed on the first side portions. The light source modules are respectively fixed on the second side portions, and each of the light source modules is used to emit lights towards one of the light guides, and outputs the lights outwardly through the one of the light guides.

In one embodiment of the present disclosure, each of the first side portions has an opening. Each of the light guides includes a light guide plate with a light-emitting front surface and a light-emitting rear surface opposite to each other where the light-emitting front surface is exposed outwards from the opening of one of the first side portions, a light incident portion extending away from the light-emitting front surface and facing towards one of the light source modules, and a diverting portion connected to the columnar body, the light guide plate and the light incident portion.

In one embodiment of the present disclosure, the light incident portion includes a plurality of protruding ribs. The protruding ribs are longitudinally arranged on the diverting portion along a long axis direction of the columnar body, and a gap is formed between any two adjacent ones of the protruding ribs.

In one embodiment of the present disclosure, each of the light source modules includes a wiring board, a plurality of colored light LEDs and a plurality of disinfection light LEDs. The wiring board is directly fixed to one of the second side portions, and a long axis direction of the wiring board is parallel to the long axis direction of the columnar body. The colored light LEDs and the disinfection light LEDs are arranged alternately on the wiring board. The colored light LEDs and the disinfection light LEDs are respectively aligned with the protruding ribs to emit towards the protruding ribs, respectively.

In one embodiment of the present disclosure, the diverting portion has a light guiding surface connecting to the light-emitting front surface and the light incident portion, and the light guiding surface is one of a planar surface and an arc surface.

In one embodiment of the present disclosure, each of the light guides includes a microstructure pattern. The microstructure pattern includes a plurality of V-shaped microstructures distributed on the light-emitting rear surface at intervals.

In one embodiment of the present disclosure, a light-emitting headphone stand is provided, the light-emitting headphone stand includes a base, a suspension portion configured for hanging a headphone thereon, a control circuit module and the columnar illumination component described above. The columnar illumination component is configured for connecting to the base and the suspension portion, respectively. The control circuit module is located within the base and electrically connected to the light source modules described above for controlling the light source modules to emit lights.

In one embodiment of the present disclosure, a light-emitting headphone stand is provided. The light-emitting headphone stand includes a base, a suspension portion configured for hanging a headphone thereon, a support frame, two light guides, two light bars and a control circuit module. The support frame is coupled to the base and the suspension portion respectively, and it has two external side surfaces and an elongated channel. The external side surfaces are opposite to one another, and the elongated channel is arranged between the external side surfaces. Each of the external side surfaces is formed with an opening. Each of the light guides includes a light-emitting front surface exposed outwards from the opening of one of the external side surfaces, a light incident portion extending away from the light-emitting front surface, and a light guiding surface connected to the support frame, the light-emitting front surface and the light incident portion. The light incident portion includes a plurality of light incident surfaces which are longitudinally arranged, and a gap is formed between any two adjacent ones of the light incident surfaces. The light bars are respectively fixed in the elongated channel.

Each of the light bars includes a plurality of colored light LEDs and a plurality of disinfection light LEDs which are respectively aligned with the light incident surfaces to emit towards the light incident surfaces, respectively. The control circuit module is located within the base and electrically connected to the light source modules described above for controlling the light source modules to emit lights.

In one embodiment of the present disclosure, the light guiding surface is one of a planar surface and an arc surface.

In one embodiment of the present disclosure, each of the light guides includes a light-emitting rear surface opposite to the light-emitting front surface, and a microstructure pattern having a plurality of V-shaped microstructures distributed on the light-emitting rear surface at intervals.

Thus, through the construction of the embodiments above, the light-emitting headphone stand of the present disclosure can achieve a thin appearance to provide double-sided light emitting functions on the columnar illumination component, thereby effectively improving product competitiveness.

The above description is merely used for illustrating the problems to be resolved, the technical methods for resolving the problems and their efficacies, etc. The specific details of the present disclosure will be explained in the embodiments below and related drawings.

BRIEF DESCRIPTION OF THE DRAWINGS

The accompanying drawings are included to provide a further understanding of the present disclosure, and are incorporated in and constitute a part of this specification. The drawings illustrate embodiments of the present disclosure and, together with the description, serve to explain the principles of the present disclosure.

DESCRIPTION OF THE EMBODIMENTS

Figure 1:
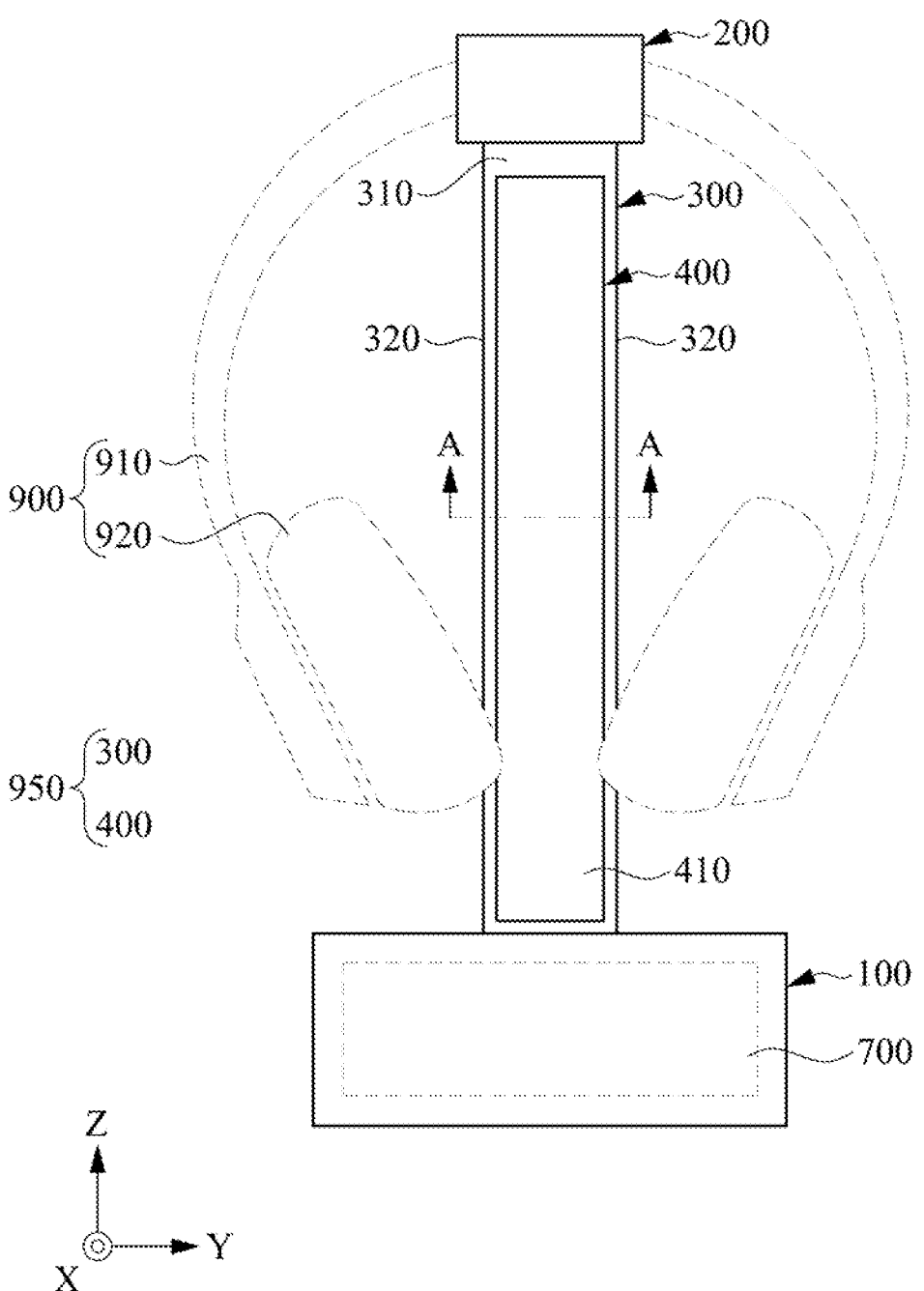
FIG. 1 is a front view of a light-emitting headphone stand according to one embodiment of the present disclosure.

Reference will now be made in detail to the present embodiments of the present disclosure, examples of which are illustrated in the accompanying drawings. Wherever possible, the same reference numbers are used in the drawings and the description to refer to the same or like parts. According to the embodiments, it will be apparent to those skilled in the art that various modifications and variations can be made to the structure of the present disclosure without departing from the scope or spirit of the present disclosure.

Figure 2:
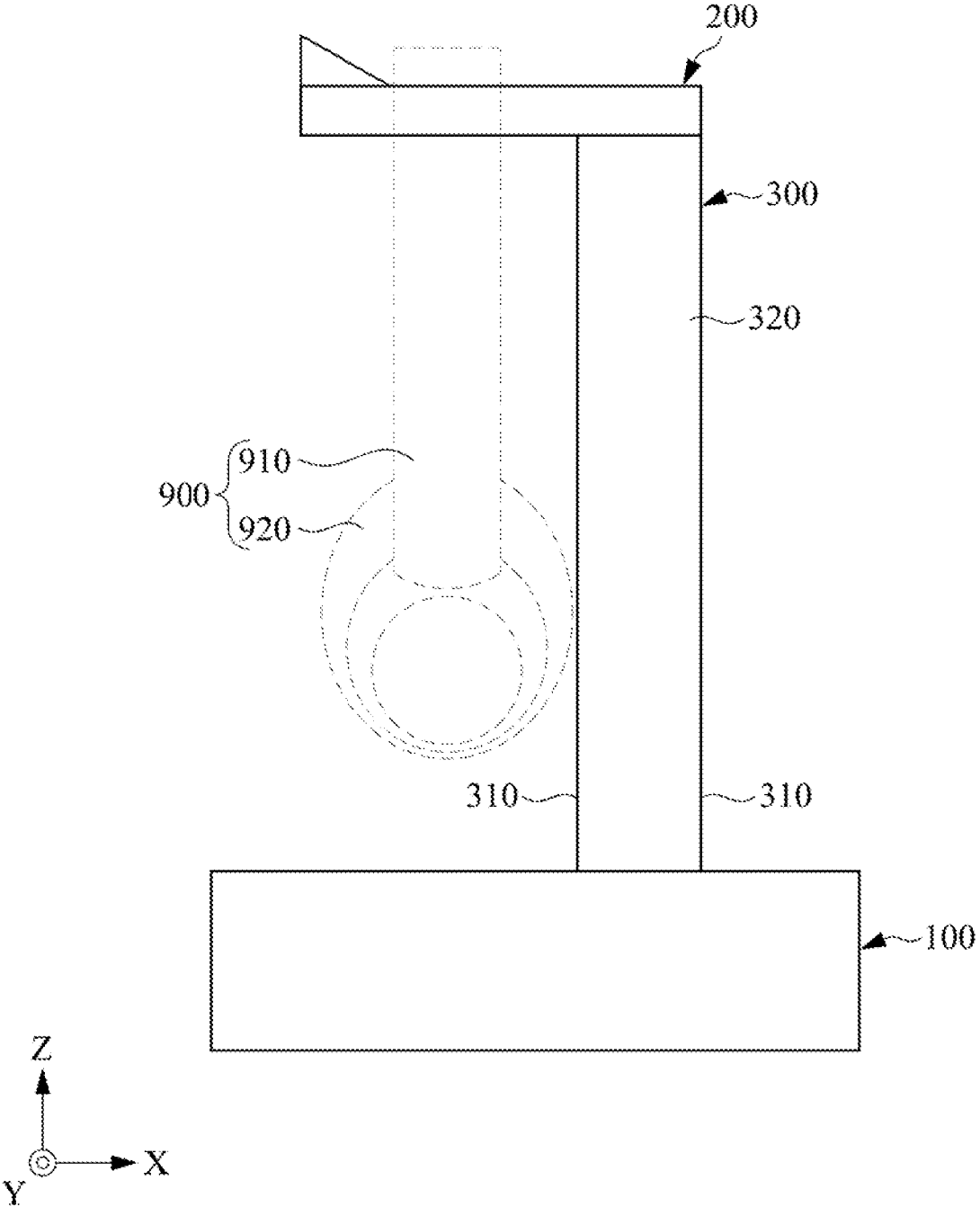
FIG. 2 is a side view of the light-emitting headphone stand of FIG. 1.
Figure 3:
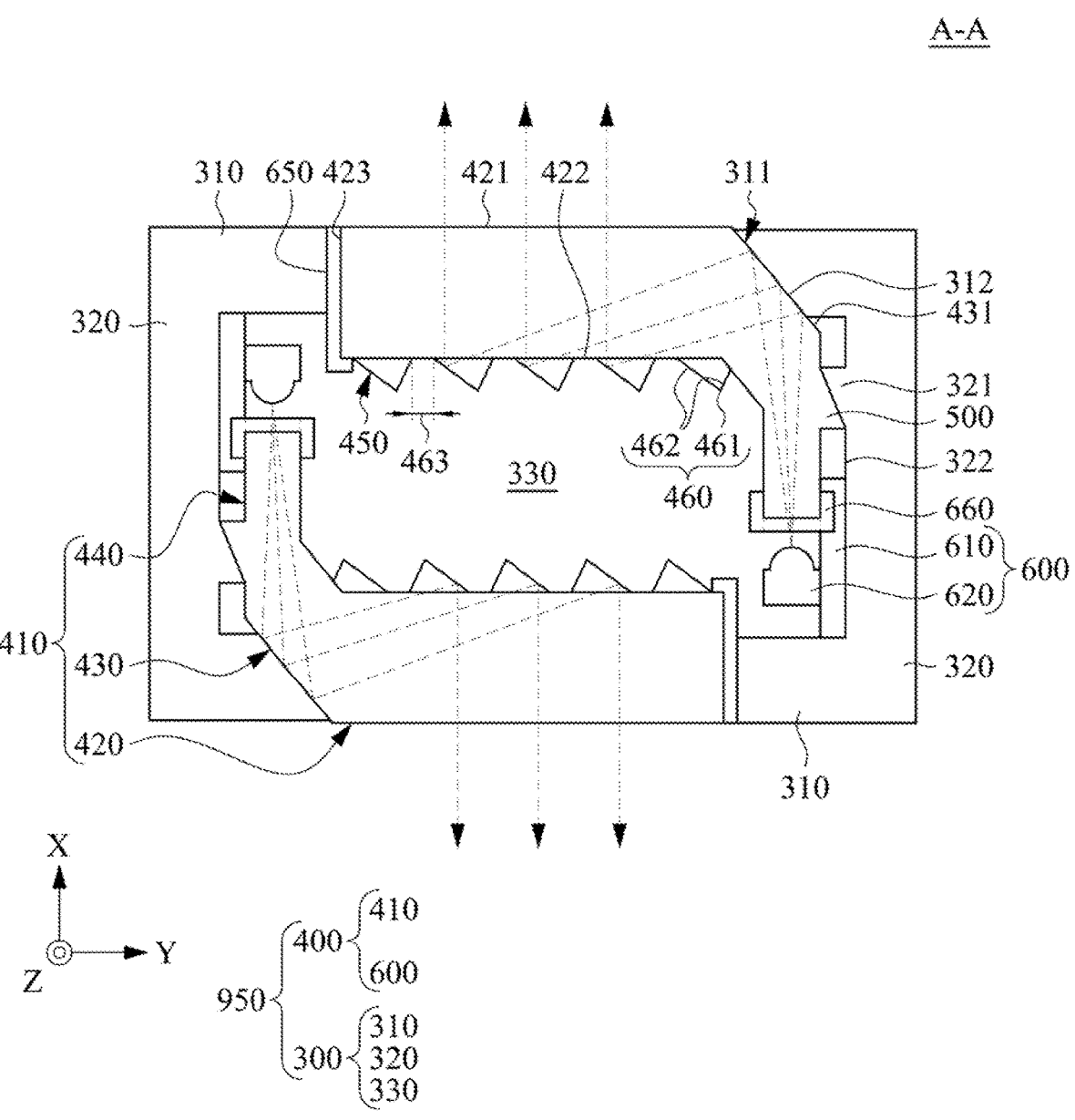
FIG. 3 is a cross-sectional view of a columnar illumination component viewed along a line AA of FIG. 1.

Reference is now made to FIG. 1 to FIG. 3, where FIG. 1 is a front view of a light-emitting headphone stand 10 according to one embodiment of the present disclosure, FIG. 2 is a side view of the light-emitting headphone stand 10 of FIG. 1, and FIG. 3 is a cross-sectional view of a columnar illumination component 950 viewed along a line AA of FIG.

1. As shown in FIG. 1 to FIG. 3, in this embodiment, the light-emitting headphone stand 10 includes a base 100, a suspension portion 200, a columnar illumination component 950 and a control circuit module 700. The base 100 is used to be placed on a plane surface (not shown in figures). The columnar illumination component 950 includes a support frame 300 and a light-emitting component 400. The support frame 300 is connected to the base 100 and the suspension portion 200, respectively.

In this embodiment, the support frame 300 is shaped as a columnar body standing on the base 100, and the suspension portion 200 is located at one end of the support frame 300 opposite to the base 100, so as to maintain a distance from the suspension portion 200 and the base 100. The light-emitting component 400 is fixedly disposed within the support frame 300 for providing bi-directional lighting outwardly from the inside of the support frame 300. The suspension portion 200 laterally extends outwards from the support frame 300 for hanging a headphone (e.g., headsets) 900 or other similar objects thereon. In specific, the headphone 900 includes a head mounting frame 910 and two earmuff portions 920 oppositely connected to the head mounting frame 910. The head mounting frame 910 can be suspended on the suspension portion 200, and each of the earmuff portions 920 is located at either side of the support frame 300 (FIG. 2).

In one embodiment, the support frame 300 is a columnar body (e.g., a rectangular column). More specifically, a housing of the support frame 300 (e.g., columnar body) includes two first side portions 310 and two second side portions 320. The first side portions 310 are opposite to each other, and the second side portions 320 are opposite to each other. Each of the first side portions 310 is disposed between the second side portions 320 and adjoined to the second side portions 320. Similarly, each of the second side portions 320 is disposed between the first side portions 310 and adjoined to the first side portions 310. An elongated channel 330 is jointly defined by the first side portions 310 and the second side portions 320 within the inner space of the support frame 300, however, the disclosure is not limited thereto. The housing of the support frame 300 can be any structure that forms the elongated channel 330 in the inner space. In one embodiment, each of the first side portions 310 is penetrated with an opening 311. The openings 311 are arranged opposite to each other to be in communication with the elongated channel 330. Each of the second side portions 320 may not have an opening, however, the present disclosure is not limited thereto.

In one embodiment, the light-emitting component 400 is fixedly located inside the elongated channel 330, and the light-emitting component 400 includes a plurality of (e.g., two) light guides 410 and a plurality of (e.g., two) light source modules 600. The light guides 410 are respectively fixed on the first side portions 310, the light source modules 600 are respectively fixed on the second side portions 320. Each of the light source modules 600 is used to emit lights towards one of the light guides 410, and outputs the lights outwardly through the light guides 410. The control circuit module 700 is located within the base 100 and electrically connected to the light source modules 600, respectively for controlling the light source modules 600 to emit lights. However, the present disclosure is not limited to the positions of the control circuit module 700 and the light source modules 600.

Figure 4:
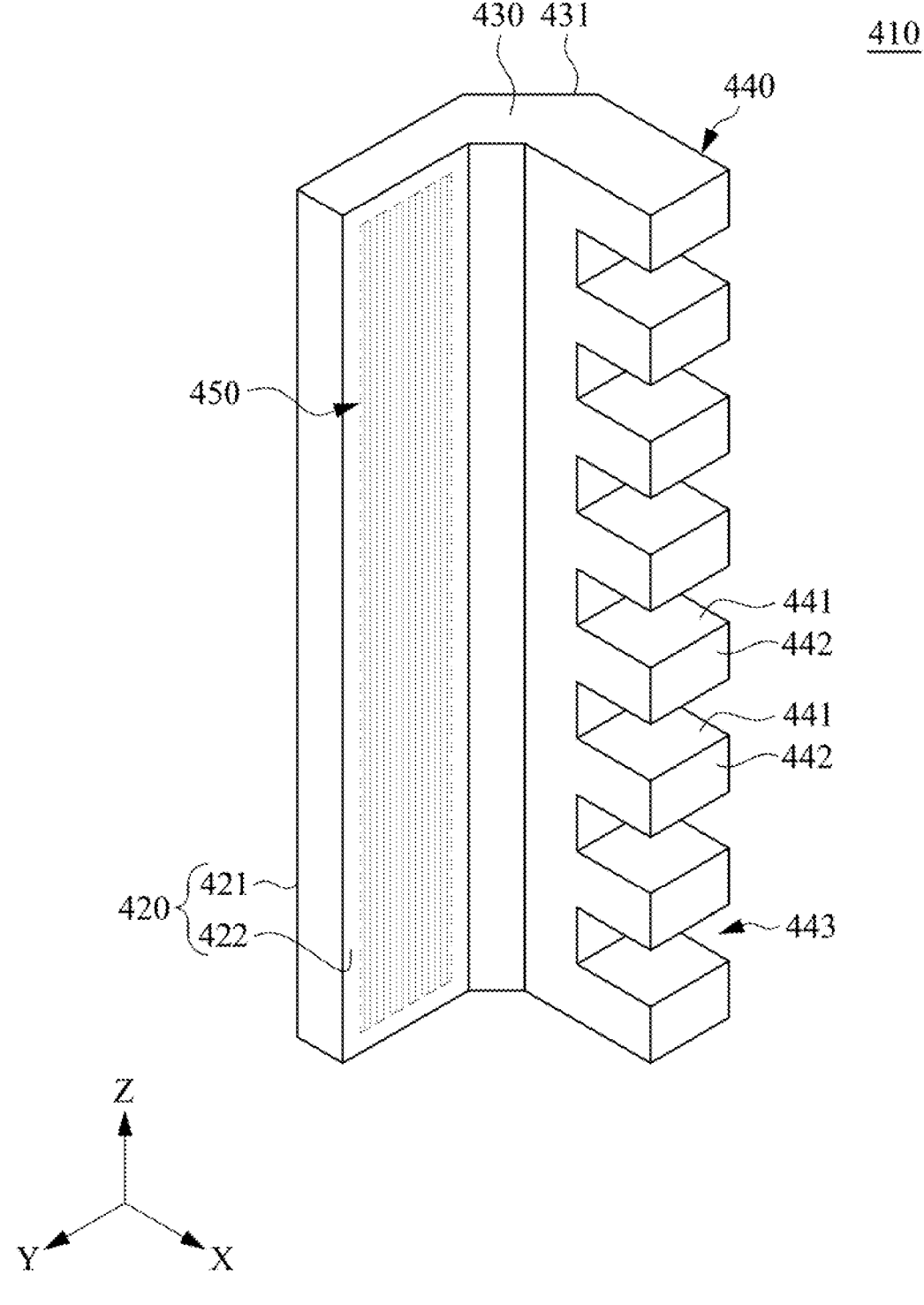
FIG. 4 is a perspective view of a light guide of FIG. 1.

FIG. 4 is a perspective view of a light guide 410 of FIG. 1. As shown in FIG. 3 and FIG. 4, each of the light guides 410 is elongated, that is, a long axis direction of each of the light guides 410 is parallel to a long axis direction (e.g., Z axis) of the support frame 300. For example, a cross-section of each of the light guides 410 is roughly shaped as an L-shape, and each of the light guides 410 includes a light guide plate 420, a diverting portion 430 and a light incident portion 440. The light guide plate 420 is provided with a light-emitting front surface 421, a light-emitting rear surface 422 and a side surface 423. The light-emitting front surface 421 and the light-emitting rear surface 422 are opposite to each other. The side surface 423 is disposed between the light-emitting front surface 421 and the light-emitting rear surface 422, and adjoined the light-emitting front surface 421 and the light-emitting rear surface 422. The side surface 423 is located on one side of the light guide plate 420 facing away from the diverting portion 430. The light guide plate 420 is located within the opening 311, wherein the side surface 423 is disposed within the opening 311, the light-emitting front surface 421 is in the opening 311 of one of the first side portions 310 to be exposed outwards from the opening 311 of the first side portion 310.

The diverting portion 430 is connected to the light guide plate 420 and the light incident portion 440 respectively so that an extension direction (e.g., X axis) of the light incident portion 440 and an extension direction (e.g., Y axis) of the light guide plate 420 are orthogonal to or at least intersected with each other. More specifically, the diverting portion 430 has a light guiding surface 431. The light guiding surface 431 is planar, and the light guiding surface 431 is connected to the light-emitting front surface 421, the support frame 300 and the light incident portion 440. The light guiding surface 431 extends along the extension direction (e.g., Z axis) of the support frame 300 (or the elongated channel 330). The light guiding surface 431 of the diverting portion 430 is located within the opening 311, and the diverting portion 430 directly abuts against a joint slope 312 of the corresponding one of the first side portions 310 with the light guiding surface 431 of the diverting portion 430.

The light incident portion 440 extends in a direction (e.g., X axis) away from the light-emitting front surface 421, and faces towards one of the light source modules 600. More specifically, the light incident portion 440 includes a plurality of protruding ribs 441, which are spaced and arranged along the long axis direction (e.g., Z axis) of the support frame 300 on the diverting portion 430. A gap 443 is formed between any two adjacent ones of the protruding ribs 441, that is, the protruding ribs 441 and the gaps 443 are longitudinally arranged on the diverting portion 430, alternatively.

Each of the protruding ribs 441 extends in a direction (e.g., X axis) away from the light-emitting front surface 421, and one end surface of each of the protruding ribs 441 facing away from the diverting portion 430 serves as a light incident surface 442. In this embodiment, the light guide plate 420, the diverting portion 430 and the light incident portion 440 are integrally formed. However, the present disclosure is not limited thereto.

Each of the light source modules 600, for example a light bar, includes a wiring board 610 and a plurality of light emitting units 620. Each of the wiring board 610 is directly fixed on one of the second side portions 320, electrically connected to the control circuit module 700 inside the base 100 (FIG. 1), and the long axis direction (e.g., Z axis) of the wiring board 610 is parallel to the long axis direction (e.g., Z axis) of the support frame 300 (or elongated channel 330). The light emitting units 620 are arranged on the wiring board

610 at intervals, and each of the light emitting units 620 emits lights towards one of the light incident surfaces 442 (FIG. 3).

Thus, when the lights of the light emitting units 620 enter the diverting portion 430 from the light incident surface 442 of the corresponding one of the light guides 410, the lights are guided into the light guide plate 420 by the light guiding surface 431 of the diverting portion 430. Next, after the lights are reflected repeatedly within the light guide plate 420, the most of the lights in the light guide plate 420 is outputted outwardly from the light-emitting front surface 421 of each of the light guide plates 420.

As shown in FIG. 3 and FIG. 4, each of the light guide plates 420 further includes a microstructure pattern 450 disposed on the light-emitting rear surface 422. The microstructure pattern 450 includes a plurality of V-shaped microstructures 460 distributed on the light-emitting rear surface 422 at intervals so as to emit lights outwards from the light-emitting front surface 421 more uniform. More specifically, each of the V-shaped microstructures 460 is shown as a V-shaped column, and a top flange 461 of the V-shaped column which is disposed away from the light-emitting rear surface 422 is linear, that is, a cross-section of each of the V-shaped microstructures 460 is in a triangular shape having two adjacent surfaces 462 and a vertex (i.e., the top flange 461) adjoined to the adjacent surfaces 462. The vertex of the triangular shape (i.e., the top flange 461) is an acute angle structure, that is, the vertex is a minor or positive angle. Each of the adjacent surfaces 462 of the V-shaped microstructures 460 is a planar surface. Any two adjacent ones of the V-shaped microstructures 460 are not connected to each other, and an interval space 463 is defined between any two adjacent ones of the V-shaped microstructures 460. The angle of the vertex (i.e., the top flange 461) of the V-shaped microstructure 460 can be adjusted arbitrarily according to restrictions or requirements.

As shown in FIG. 3 and FIG. 4, two first buckling portions (e.g., buckle slot) 321 are formed inside the support frame 300, and the first buckling portions 321 are oppositely formed on inner surfaces 322 of the second side portions 320 in the elongated channel 330. Each of the light guides 410 includes a second buckling portion (e.g., buckle) located on the light incident portion 440 (or diverting portion 430), and engaged with one of the first buckling portions 321 in order to stably fix the light guides 410 on the support frame 300.

In addition, the light-emitting component 400 further includes a plurality of (e.g., two) first positioning frames 650 and a plurality of (e.g., two) of second positioning frames 660. Each of the first positioning frame 650 is connected to one of the first side portions 310 and one of the light guide plates 420 so as to fix the corresponding light guide plate 420 to the corresponding first side portion 310. More specifically, each of the first positioning frames 650 is located on an inner wall of the opening 311 of the corresponding first side portions 310, and the first positioning frame 650 is sleeved on the side surface 423 of the corresponding light guide plate 420, so that the corresponding light guide plate 420 can be fixed within the opening 311 of the corresponding first side portions 310. Each of the second positioning frames 660 is connected to one of the light source modules 600 and one of the light incident portions 440 so as to fix the corresponding light incident portions 440 to the corresponding light source modules 600. More specifically, each of the second positioning frames 660 is fixed to the wiring board 610 of one of the light source modules 600, and sleeved on one end surface (e.g., light incident surface 442) of the light incident portion 440 facing away from the diverting portion 430, so as to position the light source module 600 on the light incident surfaces 442.

It should be noted that each second positioning frame 660, for example, has light-transmissive, or be formed with a light-transmitting opening (not shown in figures), or be misaligned with the light emitting units 620, so that the second positioning frames 660 will not prevent light from entering the corresponding light incident portion 440. In addition, each of the second positioning frames 660 may also protrude into the gaps 443 of the light incident portion 440 so as to be staggered with these protruding ribs 441 for improving the positioning strength of the second positioning frame 660 on the corresponding light guides 410.

Figure 5:
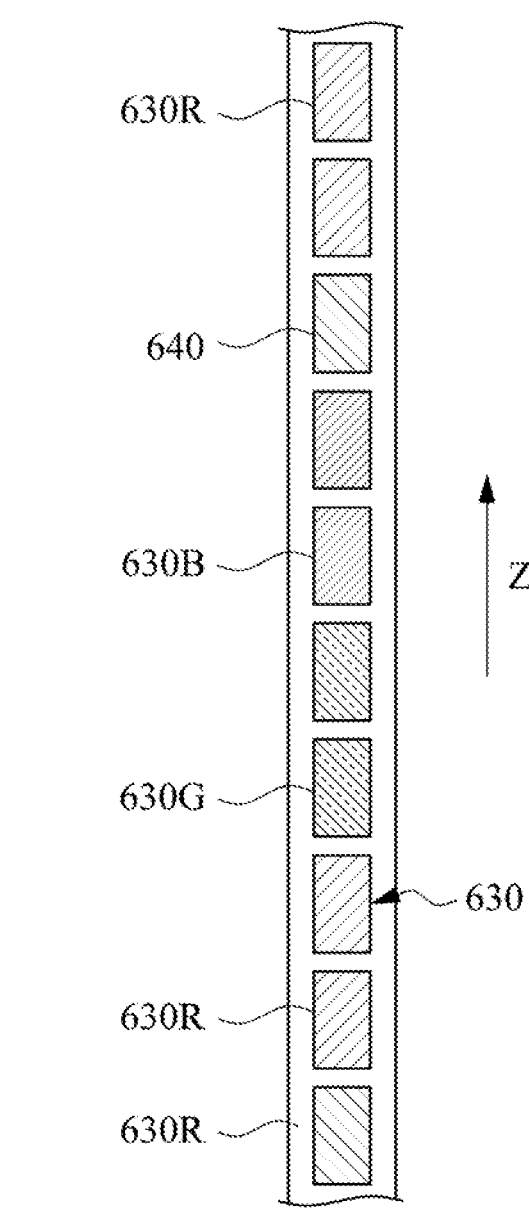
FIG. 5 is a front view of a light source module of FIG. 3.

FIG. 5 is a front view of a light source module 600 of FIG. 3. As shown in FIG. 3 and FIG. 5, in the embodiment, for example, the light emitting units 620 are divided into a plurality of colored-light light emitting diodes (i.e., colored light LEDs 630) and a plurality of ultraviolet C (UVC) light emitting diodes (i.e., disinfection light LEDs 640). The colored light LEDs 630 and the disinfection light LEDs 640 are soldered on the wiring board 610, and linearly arranged on the wiring board 610 along the long axis direction (e.g., Z axis) of the elongated channel 330 at interval. The colored light LEDs 630 and the disinfection light LEDs 640 of each of the light source module 600 are respectively aligned with and emit lights towards the light incident surfaces 442 of the protruding ribs 441, respectively. The disinfection light LEDs 640 (e.g., 6V/350 mA radiation wave 50 mW) is able to emit a UVC light.

For example, according to the mathematical formula of sterilization, a cumulative irradiation dose (mJ/cm²) is calculated out by an irradiation intensity (mW/cm²) multiplying an irradiation time (Secs). Thus, the earmuff portions 920 can be sterilized within about 2.5 minutes if the size of each of the earmuff portions 920 is about 30×30 cm². The colored light LEDs 630 are able to emit visible lights, and a light irradiation range of the colored light LEDs 630 is roughly corresponding to a light irradiation range of the disinfection light LEDs 640. In this way, the control circuit module 700 arbitrarily controls these colored light LEDs 630 or disinfection light LEDs 640 to emit lights according to restrictions or requirements.

In this embodiment, for example, each of these colored light LEDs 630 is a monochromatic LED, including one of a red LED 630R, a green LED 630G, a blue LED 630B and so on, however, the present disclosure is not limited thereto, in other embodiments, each of these colored light LEDs 630 can be modified into a red-green-blue light-emitting diode (RGB LED) integrated with a red, green and blue chip in one.

Specifically, the colored light LEDs 630 and the disinfection light LEDs 640 are arranged alternately on the wiring board 610. The colored light LEDs 630 and the disinfection light LEDs 640 are arranged on the wiring board 610 in a staggered manner, for example, in a manner of N:1 (N>=1). For example, the colored light LEDs 630 and the disinfection light LEDs 640 are arranged cyclically and sequentially on the wiring board 610 according to an arrangement rule, such as several red LEDs 630R, several green LEDs 630G, several blue LEDs 630B and a single disinfection light LED 640, however, the present disclosure is not limited to this arrangement rule, for example, only one from the two wiring boards 610 is installed with the disinfection light LEDs 640, or the disinfection light LEDs 640 are only arranged on the position of the wiring board 610 at a certain height and so on.

In this embodiment, the control circuit module 700 can control whether the colored light LEDs 630 and the disinfection light LEDs 640 emit lights. For example, more specifically, the light-emitting headphone stand 10 can be used as an atmosphere lamp which cooperates a user's usage scenarios (e.g., electronic competition or gaming), that is, the control circuit module 700 controls the colored light LEDs 630 to emit lights and the disinfection light LEDs 640 to not emit lights. On the contrary, when the light-emitting headphone stand 10 is not needed to be the atmosphere lamp, the user can use the light-emitting headphone stand 10 as an ultraviolet germicidal lamp, that is, the control circuit module 700 controls the disinfection light LEDs 640 to emit lights and the colored light LEDs 630 to not emit lights, when the user hangs up the headphones, the sterilizing lights can sterilize the earmuff portions 920. Also, the user can use the light-emitting headphone stand 10 to approach and sterilize an environmental object.

However, the present disclosure is not limited thereto. In other embodiments, the control circuit module 700 may also control the colored light LEDs 630 and the disinfection light LEDs 640 to emit lights simultaneously.

In addition, for example, the control circuit module 700 can support and cooperate the lighting effect specifications of the programmable RGB lighting controller (e.g., Chroma™ RGB, CORSAIR™ iCUE and Aura™ Sync) to control the light source modules 600 of this embodiment to provide many different lighting effects.

Figure 6A:
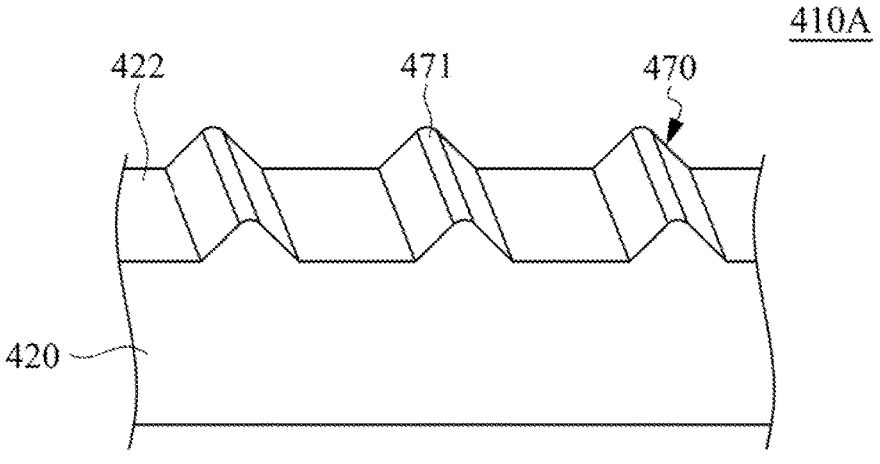
FIG. 6A to FIG. 6C are partial schematic views of V-shaped microstructures in different embodiments of the present disclosure.
Figure 6B:
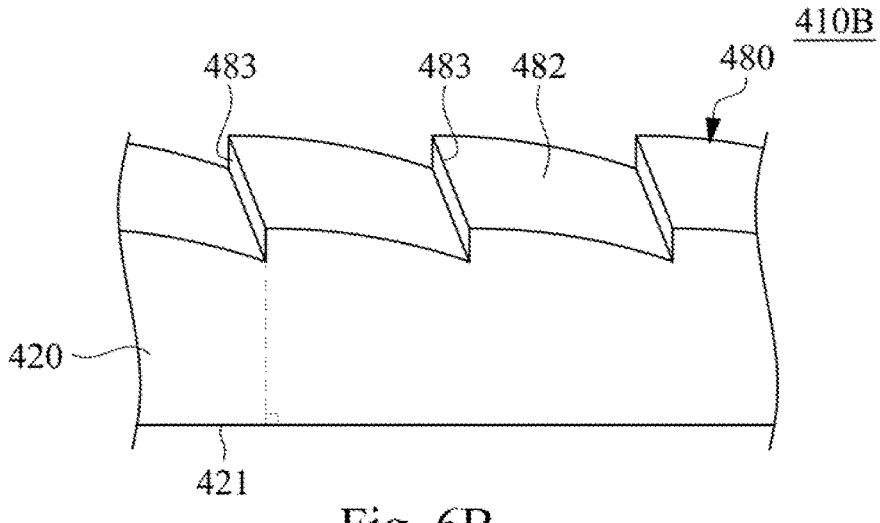
Figure 6C:
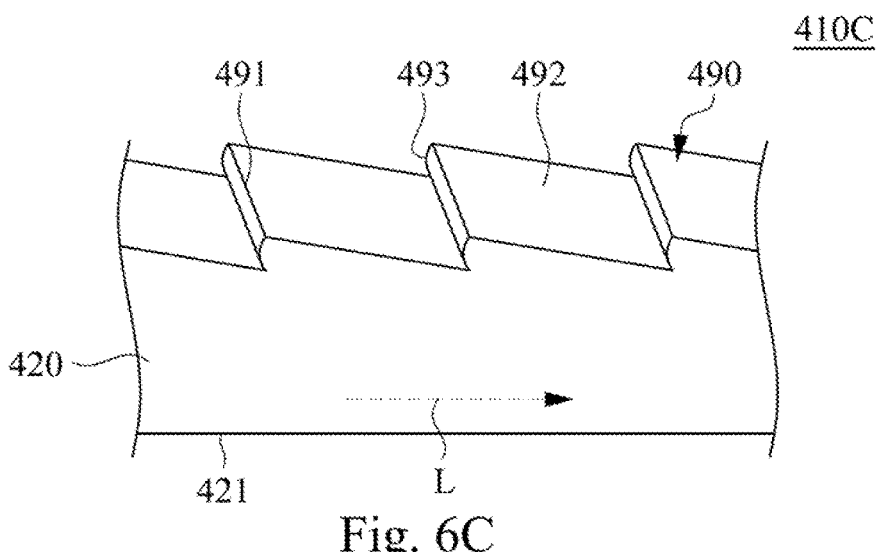

FIG. 6A to FIG. 6C are partial schematic views of V-shaped microstructures in different embodiments of the present disclosure. As shown in FIG. 6A, the light guide 410A of the present embodiment is substantially the same as the above-mentioned light guide 410, except that the vertex (i.e., the top flange 471) of the cross-section of each of the V-shaped microstructures 470 in FIG. 6A is an arc angle (i.e., radius (R) angle), rather than the acute angle structure mentioned above, however, the present disclosure is not limited thereto.

As shown in FIG. 6B, the light guide 410B of the present embodiment is substantially the same as the above-mentioned embodiment, except that the two adjacent surfaces 482, 483 of vertex (i.e., top flange 481) of each of the V-shaped microstructures 480 have different areas from each other in which one of the adjacent surfaces 482 with a larger area is an arc surface, and the other of the adjacent surfaces 483 with a smaller area is a planar surface approximately perpendicular to the light-emitting front surface 421, however, the present disclosure is not limited thereto. In addition, in FIG. 6B, any two adjacent ones of the V-shaped microstructures 480 are directly connected to each other.

As shown in FIG. 6C, the light guide 410C of the present embodiment is substantially the same as the above-mentioned embodiment, except that, in FIG. 6C, the smaller one of the adjacent surfaces 493 of the vertex (i.e., top flange 491) of the V-shaped microstructures 490 is an arc surface, and the larger one of the adjacent surfaces 492 thereof is an inclined surface, and each of the inclined surfaces (i.e., adjacent surface 492) is gradually closed to the light-emitting rear surface 422 according to the light traveling direction L, however, the present disclosure is not limited thereto.

It should be noted that those with ordinary skills in the yield of the present disclosure can correspondingly adjust and optimize one of a light incidence angle of each V-shaped microstructure, a vertex angle and the other two complementary angles of each V-shaped microstructure, a spacing between the V-shaped microstructures, a depth and a density of each V-shaped microstructure, a vertex curvature, a light guide turning angle or a curvature of each V-shaped microstructure of the above-mentioned embodiments according to specific limitations and requirements. In addition, the structure of the columnar illumination component 950 disclosed in the present disclosure is not limited to the application in the field of headphone stands. The columnar illumination component 950 can be designed with a curved or chamfered shape as required, and any device applicable to the columnar illumination component 950 totally can be applied to the structure disclosed in the present disclosure, such as various lampposts, various supporting frames, various electronic devices, vehicle bodies for bicycles, motorcycles or electric vehicles etc. however, the disclosure is not limited thereto.

Figure 7:
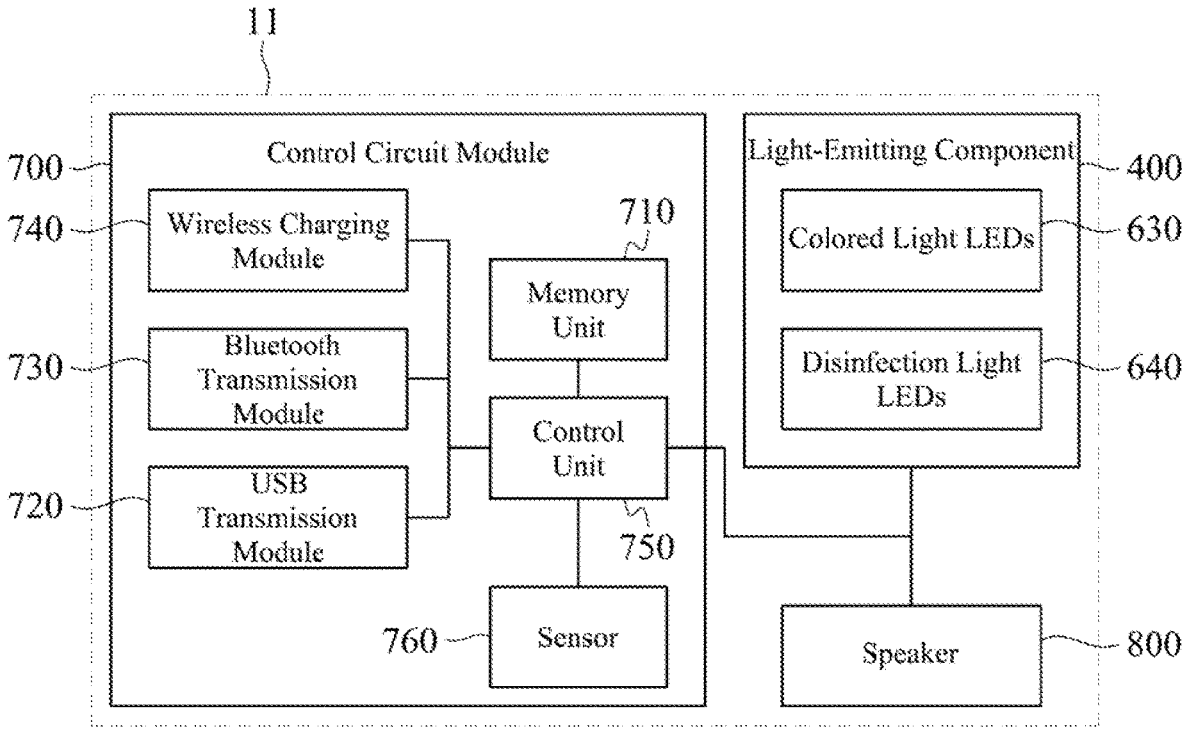
FIG. 7 is an electronic block diagram of a light-emitting headphone stand according to one embodiment of the present disclosure.

FIG. 7 is an electronic block diagram of a light-emitting headphone stand 11 according to one embodiment of the present disclosure. In this embodiment, as shown in FIG. 7, the control circuit module 700 of the present embodiment is substantially the same as that of the above-embodiment, except that the control circuit module 700 further includes a memory unit 710, one or more USB transmission modules 720, a Bluetooth transmission module 730, a wireless charging module 740 and a control unit 750. The USB transmission module 720 is used for wired signal transmission. The Bluetooth transmission module 730 is used for wireless signal transmission.

In one embodiment, the light-emitting headphone stand 11 includes a power cord for connecting an external power supply, or a USB transmission cable for receiving power. The light-emitting headphone stand 11 may also have a set of battery as a power source. The wireless charging module 740 is used for providing wireless charging service for an electronic device. The control unit 750 is electrically connected to the USB transmission module 720, the Bluetooth transmission module 730, the wireless charging module 740 and the memory unit 710 for controlling the operations of the USB transmission module 720, the Bluetooth transmission module 730, the wireless charging module 740 and the memory unit 710. For example, the control unit 750 intermittently controls these colored light LEDs 630 to emit lights according to software or firmware stored in the memory unit 710, or according to music being outputted through the USB transmission module 720, the Bluetooth transmission module 730, or other ways. In addition, the light-emitting headphone stand 11 further includes a speaker 800. The speaker 800 is, for example, a surround sound system located inside the base 100 and electrically connected to the control circuit module 700 for playing music signals from the USB transmission module 720, the Bluetooth transmission module 730 or other ways.

In one embodiment, the control unit 750 is connected to an external communication device (e.g., a computer or a smart phone) through the USB transmission module 720 or the Bluetooth transmission module 730, so as to receive a light-emitting control signal transmitted by the external communication device. The light-emitting control signal is used to control, for example, color, brightness or light-emitting time of the lights, play audio, or whether to trigger the disinfection light LEDs 640 to emit lights.

In one embodiment, the light-emitting headphone stand 11 includes a sensor 760, which is electrically connected to the control unit 750, and is able to sense whether a user is very close to the light-emitting headphone stand 11 or whether the headphone 900 is placed on the suspension portion 200. When the control unit 750 determines that the headphone 900 has been placed on the suspension portion 200 and an object (e.g., a user) is approached or not quite close to the light-emitting headphone stand 11, the control unit 750 will automatically activate the disinfection light LEDs 640 for sterilizing the headphone 900. In one embodiment, the light-emitting headphone stand 11 can be connected to an external device or sensor to receive an external sensing signal to determine whether to automatically activate the disinfection light LEDs 640 for disinfection.

Thus, through the construction of the embodiments above, the light-emitting headphone stand of the present disclosure can achieve a thin appearance to provide double-sided light emitting functions on the columnar illumination component, thereby effectively improving product competitiveness.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the present disclosure. In view of the foregoing, it is intended that the present disclosure cover modifications and variations of this disclosure provided they fall within the scope of the following claims and their equivalents.

What is claimed is:

1. A columnar illumination component, comprising:
a columnar body, having two first side portions which are opposite to each other and two second side portions which are opposite to each other, each of the first side portions that is adjoined to the second side portions and each of the second side portions that is adjoined to the first side portions, and an elongated channel that is jointly defined by the first side portions and the second side portions, each of the first side portions that is formed with an opening; and
a light-emitting component, located inside the elongated channel and including two light guides and two light source modules, where the light guides are respectively fixed on the first side portions, the light source modules that are respectively fixed on the second side portions, and each of the light source modules is used to emit lights towards one of the light guides, and outputs the lights outwardly through the one of the light guides, each of the light guides including a light guide plate with a light-emitting front surface and a light-emitting rear surface opposite to each other, wherein the light-emitting front surface is located within the opening of one of the first side portions and exposed outwards from the opening.

2. The columnar illumination component of claim 1, wherein
each of the light guides further includes a light incident portion extending away from the light-emitting front surface and facing towards one of the light source modules, and a diverting portion connected to the columnar body, the light guide plate and the light incident portion.

3. The columnar illumination component of claim 2, wherein the light incident portion comprises a plurality of protruding ribs, and the protruding ribs are longitudinally arranged on the diverting portion along a long axis direction of the columnar body, and a gap is formed between any two adjacent ones of the protruding ribs.

4. The columnar illumination component of claim 3, wherein each of the light source modules comprises:

a wiring board, directly fixed to one of the second side portions, and a long axis direction of the wiring board that is parallel to the long axis direction of the columnar body; and a plurality of colored light LEDs and a plurality of disinfection light LEDs, arranged alternately on the wiring board, wherein the colored light LEDs and the disinfection light LEDs are respectively aligned with the protruding ribs to emit towards the protruding ribs, respectively.

5. The columnar illumination component of claim 2, wherein the diverting portion has a light guiding surface connecting to the light-emitting front surface and the light incident portion, wherein the light guiding surface is one of a planar surface and an arc surface.

6. The columnar illumination component of claim 2, wherein each of the light guides comprises a microstructure pattern, and the microstructure pattern comprises a plurality of V-shaped microstructures distributed on the light-emitting rear surface at intervals.

7. A light-emitting headphone stand, comprising:

a base;

a suspension portion, configured for hanging a headphone thereon;

a columnar illumination component of claim 1, configured for connecting to the base and the suspension portion, respectively; and a control circuit module located within the base and electrically connected to the light source modules for controlling the light source modules to emit lights.

8. A light-emitting headphone stand, comprising:

a base;

a suspension portion, configured for hanging a headphone thereon;

a support frame, connecting to the base and the suspension portion respectively, and having two external side surfaces opposite to each other which are formed with an opening thereon, and an elongated channel arranged between the external side surfaces;

two light guides, each of the light guides including a light-emitting front surface located within the opening of one of the external side surfaces and exposed outwards from the opening, a light incident portion extending away from the light-emitting front surface, and a light guiding surface connecting to the support frame, the light-emitting front surface and the light incident portion, wherein the light incident portion comprises a plurality of light incident surfaces which are longitudinally arranged, and a gap is formed between any two adjacent ones of the light incident surfaces;

two light bars respectively fixed in the elongated channel, each of the light bars comprises a plurality of colored light LEDs and a plurality of disinfection light LEDs which are respectively aligned with the light incident surfaces to emit towards the light incident surfaces, respectively; and a control circuit module located within the base and electrically connected to the colored light LEDs and the disinfection light LEDs for controlling the colored light LEDs and the disinfection light LEDs to emit lights.

9. The light-emitting headphone stand of claim 8, wherein the light guiding surface is one of a planar surface and an arc surface.

10. The light-emitting headphone stand of claim 8, wherein each of the light guides comprises a light-emitting rear surface opposite to the light-emitting front surface, and a microstructure pattern having a plurality of V-shaped microstructures distributed on the light-emitting rear surface at intervals.

\* \* \* \* \*